United States Patent [19]

Lindner

[11] Patent Number: 4,911,695
[45] Date of Patent: Mar. 27, 1990

[54] PLUNGER FOR POWER-DRIVEN ANGIOGRAPHIC SYRINGE, AND SYRINGE AND POWER INJECTOR SYSTEM UTILIZING SAME

[75] Inventor: Thomas A. Lindner, West Bend, Wis.

[73] Assignee: Coeur Laboratories, Inc., Raleigh, N.C.

[21] Appl. No.: 332,709

[22] Filed: Apr. 3, 1989

[51] Int. Cl.$^4$ .............................................. A61M 5/20
[52] U.S. Cl. .................................... 604/228; 604/218; 128/655
[58] Field of Search ............... 604/187, 218, 154, 155, 604/228, 232; 128/655, 654, DIG. 1; 222/386, 326

[56] References Cited

U.S. PATENT DOCUMENTS

| | | | |
|---|---|---|---|
| 2,524,367 | 10/1950 | Smith | 604/228 |
| 2,722,215 | 11/1955 | Stig-ake Dahlgren | 604/228 |
| 3,057,351 | 10/1962 | Kimura et al. | 604/218 |
| 3,115,135 | 12/1963 | Sarnoff | 604/228 |
| 4,636,198 | 1/1987 | Stade | 604/228 |
| 4,677,980 | 7/1987 | Reilly et al. | 128/655 |
| 4,685,910 | 8/1987 | Schweizer | 604/218 |

FOREIGN PATENT DOCUMENTS

| | | | |
|---|---|---|---|
| 195026 | 1/1958 | Fed. Rep. of Germany | 604/218 |
| 2031841 | 1/1973 | Fed. Rep. of Germany | 604/228 |
| 416385 | 10/1910 | France | 604/228 |

Primary Examiner—Stephen C. Pellegrino
Assistant Examiner—Ralph Lewis
Attorney, Agent, or Firm—Steven J. Hultquist

[57] ABSTRACT

A plunger having a generally converging distal portion, and a proximal face on which is mounted a coupling structure. The coupling structure is transversely engageable by, and transversely disengageable from, a driving mechanism of a power-driven angiographic syringe, and once engaged, cannot be disengaged by rotation of the driving mechanism relative to the plunger in the absence of transverse translational movement of the driving mechanism and plunger relative to one another. The coupling structure may include a pair of laterally spaced-apart retention members, each comprising a leg rearwardly extending from the proximal face of the plunger and joined at a rearward part thereof to a laterally extending bridge segment, to the inner extremity of which is joined a pair of oppositely transversely extending flexible, resilient flange elements. The flange elements of the respective retention members thus define a transverse channel therebetween, with marginal portions thereof having reduced width dimensions relative to a medial portion thereof. Such plunger has utility in angiographic syringes of a type employed with power injector means which comprise a driving mechanism with a head engageable with the coupling structure of the plunger.

10 Claims, 3 Drawing Sheets

PLUNGER FOR POWER-DRIVEN ANGIOGRAPHIC SYRINGE, AND SYRINGE AND POWER INJECTOR SYSTEM UTILIZING SAME

BACKGROUND OF THE INVENTION

1. Field of the Invention

This invention generally relates to power-driven angiographic syringes, and specifically to a plunger for such a syringe, and to the syringe and power injector system comprising same.

2. Description of the Related Art

In the field of angiography, a contrast medium of suitable indicating character (radiopacity) is introduced under pressure into coronary arteries, and the arterial network then is monitored by fluoroscopic or other visualizing means. As a result, arterial plaque deposits and/or other arterial occlusions are readily visually determined as to their size and location, so that suitable treatment methods, such as removal of the occluding material by lasing or mechanical excision, or displacement techniques such as balloon angioplasty, may be carried out.

To effect the introduction of the contrast medium into the arterial network for angiographic study, it has been common practice to utilize injector syringes in combination with arterial catheters. The syringe may be machine-mounted in a so-called "power injector" apparatus, with the distal end of the syringe being connected to the catheter which is introduced into the arterial system to be studied.

There is disclosed in U.S. Pat. No. 4,677,980 issued July 7, 1987 to D. M. Reilly, et al, an angiographic power injector featuring a rotating turret for housing multiple angiography syringes in readiness for injection. In use, the turret is selectively rotated to align an angiographic syringe with a driving mechanism of the power injector. Specifically, as is shown in FIGS. 9 and 10 of this patent, the plunger of the angiographic syringe may be configured wit rearwardly extending hook members which are engaged by the head and stem portion (typically termed a "ram" in the field) of the driving mechanism.

In the plunger configuration disclosed in this patent, the hook elements on the proximal face of the plunger are diametrically opposed to one another, to form a slot therebetween through which the ram head is inserted and subsequently rotated, the head being of transversely extending character, so that it thereby engages the respective hook members. In this manner, the head and stem of the driving mechanism and the hook members are described to constitute a quick release driving connection, with the driving mechanism head fitting into the aperture formed by the hook members, and with the stem extending out from the aperture through the access slot between the hook members.

The Reilly et al patent, at column 6, lines 24-52 thereof, describes the subsequent operation of the coupled syringe. First, the driving mechanism is forwardly translated to drive the plunger through the syringe to expel air therefrom. Next, the syringe is connected to a source of contrast media and the driving mechanism is retracted to pull the plunger back through the syringe, to draw contrast media thereinto. Finally, the driving mechanism is advanced to drive the plunger distally in the syringe and effect injection of the contrast media through a catheter attached to the syringe. The patent states that after the injection has been carried out, the driving mechanism may be disengaged from the plunger, without reversing its movement, by the simple expedient of rotating the driving mechanism 90°, so that the driving mechanism head extends from the aperture on either side (see FIG. 10 of the patent). Subsequent retraction of the driving mechanism results in the head and stem of the driving mechanism being withdrawn from the aperture and slot thereby disengaging he driving mechanism from the plunger.

As a result of the foregoing configuration of the driving mechanism, and the hook members on the plunger, the risks incident to retracting the plunger through the syringe during the angioplasty procedure are said to be eliminated, and the mating hook members and driving mechanism head are said to cooperate so that the plunger can be placed in either a driven retractable state, or an undriven non-retractable state, at any time during the injection operation and at any position of the plunger, without substantial force being applied therebetween.

While the foregoing configuration of the hook members on the plunger facilitates the engagement and disengagement of the driving mechanism, without change in the position of the plunger, it also is true that the hook members themselves provide only a very small contact area for mating with the head of the driving mechanism, when the driving mechanism is in driving or retraction engagement with the hook members.

There is thus the danger that the head of the driving mechanism may disengage from contact with the hook members during operation of the syringe, so that subsequent rotation of the driving mechanism to effect disengagement actually effects re-engagment of the driving mechanism with the hook members, in turn causing retraction of the plunger, an occurrence which specifically is desired to be avoided.

The Reilly et al patent discloses other plunger and driving mechanism constructions, e.g., as shown in FIGS. 11-21 of the patent, but all such alternative constructions are relatively more complex in construction and operation.

Prior copending U.S. patent application No. 07/299,974 filed Jan. 19, 1989 in the names of L. L. Densmore and T. A. Lindner, discloses an angiographic syringe plunger having a generally converging distal portion, and a rear face on which is provided a coupling structure which is transversely engageable by, and transversely disengageable from, a driving mechanism of a power-driven angiographic syringe. Once engaged by the driving mechanism, the plunger cannot be disengaged solely by rotation of the driving mechanism relative to the plunger in the absence of translational movement of the driving mechanism and plunger relative to one another. The coupling structure disclosed in this application includes a wall extending rearwardly from the proximal face of the plunger body and partially circumferentially thereon. The wall terminates at a proximal extremity, and a radially inwardly extending flange is joined at a outer peripheral portion thereof to the proximal extremity of the wall. In such manner, the radially inwardly extending flange and the wall form with the proximal face of the plunger a cavity transversely open to insertion of a ram head thereinto.

For example, the coupling structure described in this prior copending application may be generally C-shaped, with a continuously curved portion having an arc length not exceeding about 180°, and optionally provided with tangentially extending end segments respectively joined to the extremities of the continuously curved portion.

A disadvantage of the plunger construction described in copending U.S. patent application No. 07/299,974 is that the coupling structure thereof has a "directional" character, in that the plunger proximal face must be rotationally aligned with the head of the driving mechanism, to permit lateral engagement of the driving mechanism head with the cavity which is defined by the coupling means with the proximal face of the plunger. A corresponding orientation of the plunger and coupling mechanism likewise is required for lateral disengagement of the driving mechanism head from this cavity. As a result, this prior application discloses the use of registration marks on the plunger, for alignment thereof with a corresponding alignment mark on the carrousel of the power injector system (see, for example, FIG. 7 of this prior copending application, the disclosure of which hereby is incorporated herein by reference).

Even with such a registration system, however, the turret or carrousel arrangement employed on angiograpic syringe power injector systems necessitates that the ram access the plunger from two opposing directions. In other words, as the ram head is disengaged from the plunger of a first angiographic syringe in the carrousel, the carrousel is rotated to access a second angiographic syringe for engagement by the ram head. Since the ram head is engaging the respective first and second angiographic syringes from opposite directions, the plungers must be correspondingly "faced" in the proper engagement direction.

The directional difficulties associated with the provision of a multiplicity of angiographic syringes on a carrousel of a power injector system may thus be overcome by the above-described provision of alignment marks on the plunger and carrousel, however it may be difficult in practice to achieve the precise registration of alignment marks required for the effective use of the power injection system, particularly in use environments in which time is of critical importance.

Accordingly, it is an object f the present invention to provide a plugger which is readily engageable with the driving mechanism of a power injector system from both of two opposing directions.

It is another object of the present invention to provide an angiography syringe comprising such a plunger.

It is a further object of the present invention to provide an angiography power injector system comprising an angiography syringe including such a plunger.

Other objects and advantages of the present invention will be more fully apparent from the ensuing disclosure and appended claims.

SUMMARY OF THE INVENTION

In one aspect, the present invention relates to a plunger having utility in a power-driven angiographic syringe assembly comprising power driving means including an axially extending driving shaft and a transversely extending driving head attached to the shaft.

The plunger includes a plunger body having a generally convergent distal portion and a proximal face.

Laterally spaced-apart retention members are disposed on the proximal face e.g., in diametrally opposite relationship to one another on the proximal face, for retaining the power driving means in position once engaged with the plunger. Each retention member comprises a leg portion extending generally rearwardly (proximal) from the proximal face and joined at a rearward part thereof to a bridge segment laterally inwardly extending therefrom toward the other retention member, to an inner extremity, which is in spaced relationship to the corresponding inner extremity of the bridge segment of the other retention member.

The inner extremities of the bridge segments thereby define a spacing accommodating transverse passage of the drive shaft therethrough. The leg portions and bridge segments of the retention members corporately define with the proximal face of the plunger a lateral slot accommodating transverse passage of the driving head therethrough.

Transversely outwardly extending flexible, resilient flange elements are joined to the inner extremity of each of the aforementioned bridge segments and form laterally spaced-apart, transversely aligned pairs of flange elements on either side of the bridge segments, defining a transverse channel therebetween. The flange elements are shaped to define marginal portions of the transverse channel having a reduced channel width relative to a medial portion thereof. The marginal channel portions allow transverse passage of the drive shaft therethrough by deformation of the flange elements bounding the marginal channel portions so that the drive shaft thereafter is retentively held in the medial portion of the transverse channel to accommodate free rotation of the driving mechanism relative to the plunger without disengagement of the driving mechanism therefrom.

The invention relates in another aspect to an angiographic syringe comprising a plunger of the above-described construction.

In a still further aspect, the invention relates to a power injector system comprising an angiographic syringe including a plunger of the above-described construction.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
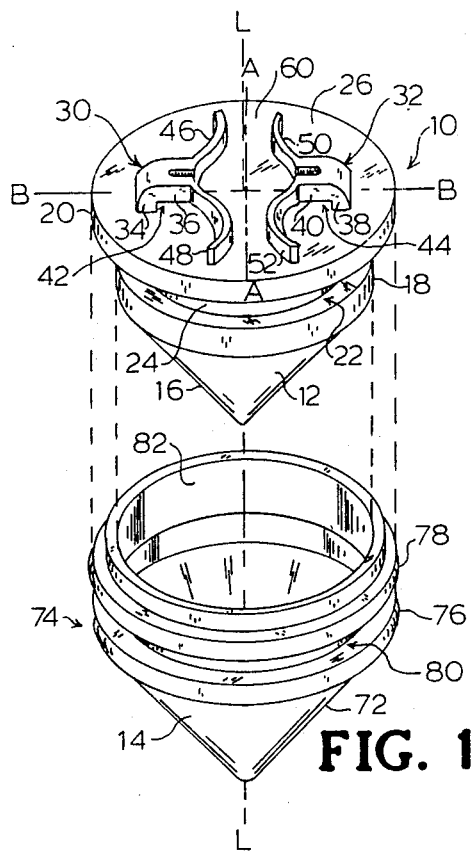
FIG. 1 is an exploded perspective view of a plunger according to one embodiment of the present invention.

Referring now to the drawings, there is shown in FIG. 1 a perspective view of a plunger 10 in accordance with one embodiment of the present invention. The plunger as illustrated comprises a plunger body 12 and a frontal sheath 14.

The plunger body 12 has a conical distal end portion 16 extending proximally to a distal cylindrical portion 18, rearwardly of which is provided a cylindrical proximal portion 20. The respective distal and proximal cylindrical portions 18 and 20 of the plunger body are in axial spaced relationship to one another. Between the respective cylindrical portions 18 and 20 is a groove 22, having an interior surface defined by the intermediate cylindrical portion 24 of the plunger body. The central axis of the plunger assembly as shown in FIG. 1 is indicated by line L—L.

The proximal cylindrical portion 20 of the plunger body 12 features a proximal face 26 which preferably is generally planar as shown.

Reposed on the proximal face 26 is a coupling structure comprising power driving means (ram) retention members 30 and 32, which as shown are symmetrically disposed on the proximal surface 26, diametrally opposite and laterally spaced apart from one another, in symmetrical relationship to the central axis L—L of the plunger.

With regard to retention member 30, the same comprises a leg portion 34 extending generally rearwardly from the proximal face 26 and joined at a rearward part thereof to a bridge segment 36 which laterally inwardly extends from the rearward part of the leg portion 34 toward the other retention member 32, which is similarly constructed with leg portion 38 and bridge segment 40. The inner extremities of the respective bridge segments 36 and 40 of the laterally opposed retention members are thus in spaced relationship to one another to accommodate transverse passage of the drive shaft of a driving mechanism therethrough.

For ease of descriptive reference in the ensuing discussion, the term "transverse" will generally refer to the direction of engagement of the power driving means (ram) with the plunger, and the direction of disengagement therefrom. In FIG. 1 this direction is generally indicated by the transverse line A—A. The transverse dimension thus is generally perpendicular to the central axis L—L of the plunger, as illustrated. The term "lateral" as used herein refers to a direction which is generally perpendicular to the transverse direction as well as to the axis L—L, and is indicated in FIG. 1 by the lateral line B—B.

The leg portion 34 and bridge segment 36 of retention member 30 defines with the proximal face 26 of the plunger a slot 42. Correspondingly, the leg portion 38 and bridge segment 40 of retention member 32 defines with the proximal face 26 a slot 44. There is thus define an overall laterally extending slot comprising slot segments 42 and 44 which accommodates transverse passage of the driving head of the driving means therethrough.

At the inner lateral extremity of bridge segment 36 of retention member 30 is joined transversely outwardly extending flange elements 46 and 48. Retention member 32 is similarly configured, with transversely outwardly extending flange elements 50 and 52 joined to the inner lateral extremity of bridge segment 40. The respective flange elements 46, 48, 50 and 52 are formed of a flexible, resilient material accommodating lateral deformation of these flange elements, as hereinafter more fully described.

The plunger construction shown in FIG. 1 provides transversely aligned pairs of the laterally spaced-apart flange elements, viz., a first flange element pair comprising flange elements 46 and 50, and a second flange element pair comprising flange elements 48 and 52, on the respective sides of the bridge segments. In such manner, the paired flange elements bound and define a transverse channel 60 therebetween.

The plunger body 12 may be formed, if desired, with a central cavity therein (not shown), as described in the aforementioned prior copending U.S. patent application No. 07/299,974, to minimize weight and material requirements for the plunger, as well as to facilitate molding, by providing faster mold cycling times, when the plunger body is formed of a molded material.

The distal sheath 14 of the plunger is adapted to fit matingly over the distal conical portion 16, and the respective distal and intermediate cylindrical portion 18 and 24, of the plunger body. The distal sheath preferably is formed of a resilient material, of sufficient intrinsic lubricity or amenability to lubrication, to yield it slidingly engageable with the inner wall surface of a syringe in which the plunger is deployed.

The distal sheath 14 comprises distal conical portion 72 and a proximal portion 74 whose outer surface describes axially spaced-apart ridges 76 and 78 bounding a groove 80 therebetween.

The sheath wall is of generally uniform thickness along the conical distal portion 72. At its rearward extremity the sheath wall forms a radially inwardly extending flange 82 which mates cooperatively with the groove 22 of the plunger body, when the sheath and body of the plunger are cooperatively mated with one another.

In general, the plunger body 12 may be formed of any suitable material of construction which is advantageously employed in the use environments of the plunger and syringe with which the plunger may be associated. The plunger body may for example be formed of a generally stiff, resilient material, such as a hard elastomer, or alternatively, it may be formed of any other suitable natural or synthetic, polymeric or non-polymeric, materials. In practice, plastics generally are preferred materials of construction. A polymeric material which may be employed to good advantage in such plunger body is polyphenylene oxide, such as the polyphenylene oxide material commercially available from General Electric Company, Pittsfield, Mass., under the trademark Valox®. The plunger sheath 14 likewise may be formed of any suitable material which is advantageously employed in the use environments of the plunger and syringes with which same is associated. Preferred materials of construction include rubber materials, with natural rubber typically being the most preferred. The sheath is suitably flexible, resilient, and elastomeric in character, to accommodate mating with the plunger body in a manner ensuring that the sheath is retained in position on the plunger body during the use of the plunger.

The retention members 30 and 32 may be formed of any suitable materials of construction, with the proviso that the flange elements 46, 48, 50, and 52 must be flexible and resilient in character, to accommodate deformation thereof during the engagement and disengagement of the drive means during the use of the plunger in a power-driven angiographic syringe system. Accordingly, the retention members 30 and 32 may be formed of the same material of construction as the plunger body 12, if such material provides the requisite structural integrity in the plunger body and leg portions and bridge segments of the coupling structure, while concomitantly providing sufficient flexibility and resilience in the flange elements 46, 48, 50, and 52.

In this respect, the retention members 30 and 32 may be formed integrally with the plunger body 12, such as by injection molding, machining, or other suitable forming method(s). Alternatively, the retention members 30 and 32 may be formed separately from the plunger body, and affixed thereto at the lower extremities of the respective leg portions 34 and 38 by any suitable means or methods efficacious for such securement, e.g., adhesive bonding, ultrasonic welding, fusion bonding, mechanical fastening, etc.

As a further alternative, the flange elements may be formed separately from the leg portions and bridge segments of the respective retention members, or any two of such elements may be formed separately from the third, and correspondingly joined in any suitable manner. For example, the leg portions and bridge segments of the respective retention members may be integrally molded from a suitable plastic material with the plunger body and subsequent to such formation, flange elements 46, 48, 50, and 52 may be suitably attached to the inner lateral extremities of the corresponding bridge segments.

Figure 2:
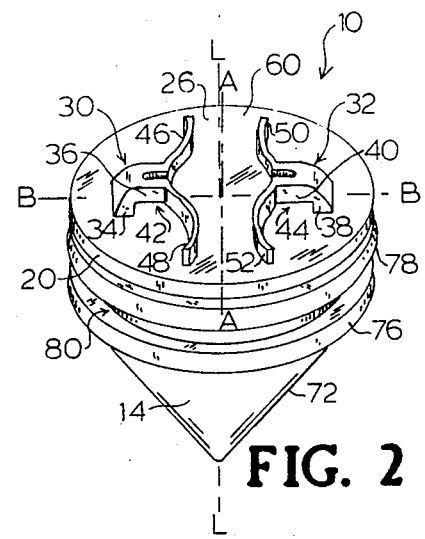
FIG. 2 is a perspective view of a plunger, corresponding to the plunger construction shown in FIG. 1, as assembled.

A perspective view of a plunger, as assembled from the sheath and body components of FIG. 1, is shown in FIG. 2, wherein all parts and elements are numbered correspondingly with respect to the same or corresponding features in FIG. 1.

Figure 3:
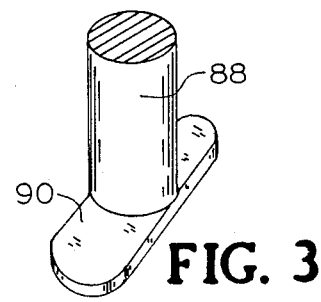
FIG. 3 is a perspective view of a portion of a driving mechanism, such as may be employed with the plunger of the present invention.

FIG. 3 is a perspective view of a portion of a driving mechanism including an axially extending shaft 88, joined at its lower extremity (in the position shown) to a driving head 90. The drive shaft 88 and driving head 90 corporately are referred to herein as the "ram" of the power injector system.

Figure 4:
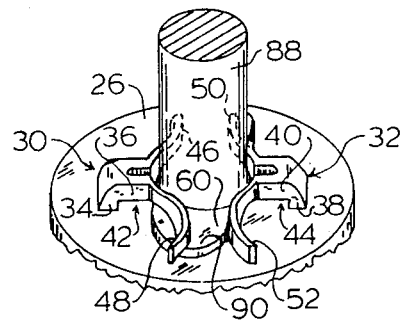
FIG. 4 is a perspective view of the driving mechanism of a power injector, as engaged with the coupling means on the proximal face of a plunger according to one embodiment of the present invention.

FIG. 4 is a perspective view of a proximal surface portion of a plunger according to one embodiment of the present invention, with the coupling means on proximal face 26 engaged with the ram comprising shaft 88 and driving head 90. In the FIG. 4 drawing, all parts and features are numbered correspondingly with respect to FIGS. 1-3 herein.

In the FIG. 4 engaged plunger assembly, the shaft 88 of the ram is engaged in a central (medical) portion of the transverse channel 60 which is bounded by the respective flange elements 46, 48, 50, and 52. These flange elements are joined to the corresponding bridge respective retention members 30 and 32.

As previously described, retention member 30 comprises a leg portion 34 joined to a laterally extending bridge segment 36, to the innermost lateral extremity of which are joined transversely outwardly extending flange elements 46 and 48, in the previously described manner.

Correspondingly, retention member 32 comprises leg portion 38, which is joined at rearward part thereof to laterally extending bridge segment 40. Flange elements 50 and 52 are joined at their respective transversely inner extremities to the lateral inner extremity of the bridge segment 40.

Figure 5:
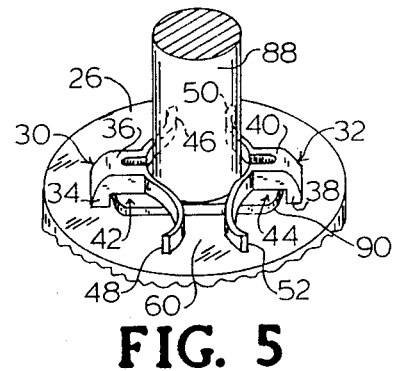
FIG. 5 is a view of a portion of the driving mechanism of a power injector system, engaged with the coupling structure on the proximal face of a plunger according to one embodiment of the present invention, such view corresponding to that shown in FIG. 4, but with the head of the driving mechanism being rotated by 90° from the position shown in FIG. 4.

FIG. 5 is a corresponding view of the FIG. 4 engaged plunger assembly, wherein all parts and features are correspondingly numbered, but wherein the shaft 88 has been rotated by 90° relative to the position shown in FIG. 4. As shown, the retention members 30 and 32 are dimensionally sized and shaped to accommodate free rotation of the driving head 90 incident to rotation of driving shaft 88, with the provision of a laterally extending slot comprising slot segments 42 and 44 between the proximal face 26 of he plunger and the respective leg portions and bridge segments of the retention members.

Figure 6:
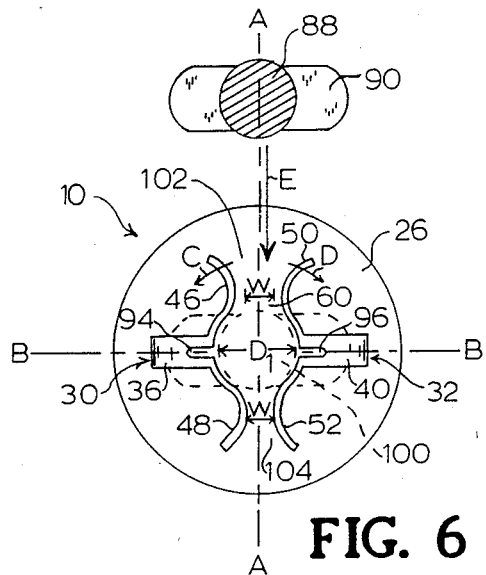
FIG. 6 is a side elevation view, in partial cross-section, of an angiographic syringe comprising a plunger according to one embodiment of the present invention, in operative engagement with power injector means.

FIG. 6 is a top plan view of the proximal surface 26 of the plunger according to one embodiment of the present invention featuring a coupling structure mounted on the proximal face including retention members 30 and 32. The proximal face of the plunger and the coupling structure thereon are shown in associative relationship with a ram comprising driving shaft 88, to which is joined a driving head 90 in the manner shown and described with reference to FIG. 3 herein. The ram and plunger shown in FIG. 6 are numbered correspondingly with respect to FIGS. 1-5 herein.

As shown, the flange elements 46 and 48 are joined at their inner transverse extremities to the bridge segment 36 of retaining member 30. In like fashion, flange elements 50 and 52 are joined at their inner transverse extremities to bridge segment 40 of retaining member 32. The respective bridge segments 36 add 40 may, as shown, be formed with laterally extending cavities 94 and 96, respectively, to enhance the flexible and resilient character of the flange elements attached thereto. Thus, the respective retention members 30 and 32 may be configured with a flattened "wishbone" shape as shown in the plan view illustrated.

In the FIG. 6 drawing, the respective flange elements 46, 48, 50, and 52 corporately bound and define a transversely extending channel 60 (the transverse center line A—A of such channel being shown for ease of reference).

The transverse channel 60 comprises a medial portion 100, and marginal portions 102 and 104. In the marginal portions of the transverse channel, the overall flattened W-shape of the respective pairs of flange elements transversely bounding the channel 60 (viz., flange elements 46 and 48 as a first pair, and flange elements 50 and 52 as a second pair) provides a channel configuration wherein the marginal channel portions 102 and 104 are of reduced channel width relative to the medial portion 100 of the channel.

Thus, the marginal portion 104 of the passage 60 defines a channel width at the point of closest proximity of the respective facing flange elements 48 and 52 which is denoted as dimension W in the FIG. 6 drawing.

At the opposite end of the transverse channel, at the marginal portion 102 thereof, the normal width dimension W of such portion of the channel is indicated, with the respective facing flange elements 46 and 50 bounding such marginal portion of the channel being laterally displaced in the direction of arrows C and D, respectively, to indicate the deformation of these flange elements which occurs when the driving means comprising driving shaft 88 and driving head 90 is translated in the transverse direction indicated by arrow E for engagement with the retention members.

Accordingly, the driving mechanism is engaged with the plunger 10 by translating the driving means comprising shaft 88 and head 90 in the direction of arrow E along transverse center line A—A, to cause same to pass successively through the marginal portion 102 of the transverse channel 60 to the medial portion 100 thereof, to finally repose in the position indicated in dotted line outline, on which the diameter of the driving shaft 88 is indicate as dimension $D_1$.

After passage of shaft 88 through marginal portion 102 of the transverse channel 60 to the medial portion 100 thereof the facing flange elements 46 and 50 bounding marginal portion 102 of the channel will of course return to their normal configuration defining a spacing width W, by lateral return movement of these respective flange elements in directions opposite to those indicated by arrows C and D in the drawings.

Once the driving mechanism comprising shaft 88 and head 90 is reposed in the medial portion 100 of the transverse channel 60, it will be apparent that the driving mechanism thereafter is non-disengageable from the plunger by simple rotation of the driving head relative to the plunger. Accordingly, it is possible to disengage the driving mechanism from the plunger, once engaged therewith, only by transverse translation of the driving mechanism relative to the plunger, i.e., translation of the driving mechanism in a direction along transverse center line A—A. It will also be appreciated that the driving mechanism may be thus disengaged from the plunger in both transversely opposite directions. In other words, the driving mechanism, once reposed in the medial portion 10 of the transverse channel, can be disengaged from the plunger by either transverse translation through the marginal channel portion 102, or by transverse translation of the driving mechanism through marginal channel 104.

Accordingly, the bi-directional character of the driving mechanism engagement and retention means in the plunger of the present invention overcomes the difficulties associated with the directional character of the plunger disclosed in prior copending U.S. patent application No. 07/299,974 filed Jan. 19, 1989.

Figure 7:
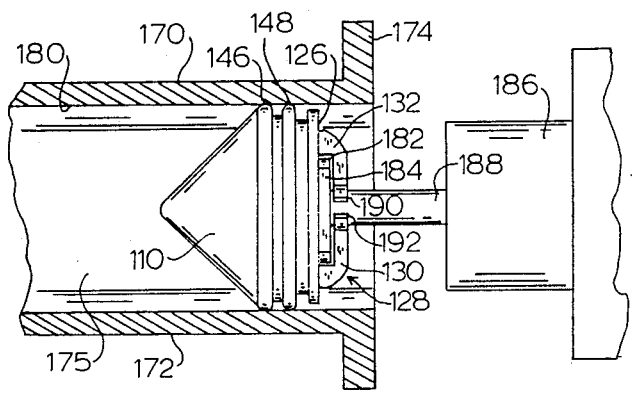
FIG. 7 is a top plan view of the proximal surface of a plunger according to one embodiment of the present invention, shown with the associated portion of a power injector system, to illustrate the coaction therebetween.

FIG. 7 is a side elevation view, in partial section, showing an angiograhic syringe comprising the plunger of the present invention, add an associated part of the driving mechanism of an angiography power injector system, in engagement with the plunger.

The angiographic syringe 170 comprises a generally cylindrical barrel 172, which terminates at its proximal end in a circumferentially continuous, radially extending flange 174.

The plunger 110 is reposed in the interior volume 175 of the angiographic syringe 170, with the ridges 146 and 148 of the plunger sheath being in contact with the inner wall surface 180 of the angiographic syringe.

The plunger comprises a coupling structure 128 as previously described in FIGS. 1-6 hereof, with the retention members 130 and 132 corporate defining with the rear face 126 of the plunger a cavity 182. The cavity 182 is constructed and arranged for transversely receiving the head 184 of the driving mechanism 186. Flange elements 190 and 192, together with corresponding flange elements on the opposite side of the plunger from that shown, corporately define a transversely extending channel into which the head 184 and shaft 188 of the driving mechanism are transversely inserted for engagement with the plunger, and from which the head and shift of the driving mechanism are transversely withdrawn for disengagement from the plunger, as previously described. The driving head 184 thus is mounted on the axially extending drive shaft 188, and the driving mechanism comprises means (not shown) for axially extending or retracting the shaft 188 and head 184 as desired.

Figure 8:
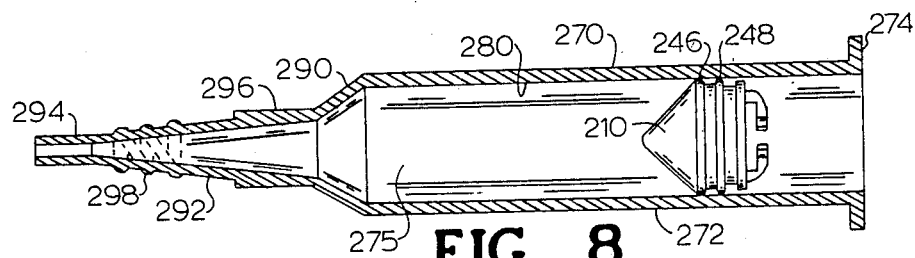
FIG. 8 is a side elevation view, in partial section of an angiographic syringe according to one embodiment of the present invention, comprising a plunge in accordance with the present invention.

FIG. 8 is a side elevation view, in section, of an angiographic syringe according to one embodiment of the present invention, comprising a plunger of the type shown in FIGS. 1-7 hereof.

As illustratively shown in FIG. 8, the angiographic syringe 270 comprises a generally cylindrical barrel 272 enclosing an interior volume 275 in which the plunger 210 is slidably mounted, in engagement, at ridges 246 and 248, with the inner wall surface 280 of the syringe barrel. The syringe barrel terminates at a proximal end in radially outwardly extending flange 274. At its distal end, the syringe barrel 272 is joined via a frustoconical section 290 to distal tapered section 292, which in turn is joined at a distal extremity thereof to the tubular discharge section 294. The tapered section 292 of the syringe optionally features, at a proximal portion thereof, a plurality of vanes 276, which may be employed for positive locking of the syringe in the mounting structure of a power injector system. The tapered section 292 features o a distal portion of its exterior surface a threading 298, by means of which the angiographic syringe may be coupled, via a suitable complimentarily threaded connecting fitting, to an angiography catheter (not shown).

Figure 9:
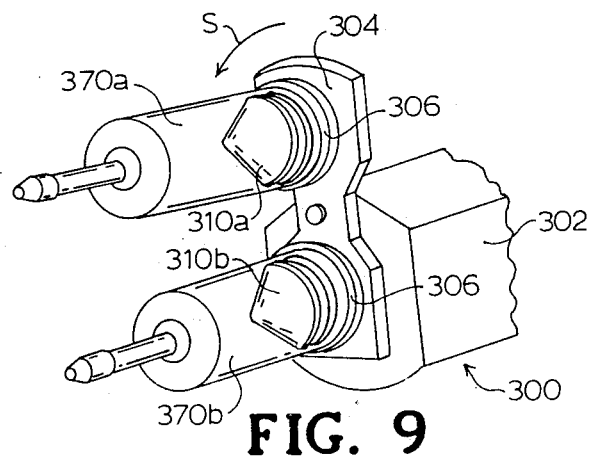
FIG. 9 is a partial perspective view of a power injector device featuring a rotatable carousel mounting two angiographic syringes in accordance with the present invention.

FIG. 9 is a perspective view of an angiography injection system 300 including power injector 302. The power injector comprises a carrousel 304 mounted for rotation, e.g., in the direction indicated by arrow S in FIG. 9, and contains openings bounded by collars 306 through which syringes 370a and 370b are inserted. As shown in FIG. 9, the lower syringe 370b has been placed, by selective adjustment of the carrousel, in engagement position with the driving mechanism of the power injector 302, so that the plunger 310b of syringe 370b is in engagement with the head and shaft of the driving mechanism. Concurrently, the angiographic syringe 370a, comprising plunger 310a, is mounted in position on the upper segment of the carrousel, for subsequent translation into alignment with the power injector driving mechanism, and concurrent disengagement of the plunger 310b of syringe 370b therefrom.

As an illustrative example of an embodiment of the plunger of the invention, such as may be usefully employed with a 150 milliliter angiographic syringe, the plunger, of a type as shown in the respective drawings of FIGS. 1-9 hereof, may have a body formed of Valox ® polyphenylene oxide (General Electric Company, Pittsfield, Mass.) and a sheath of natural rubber. The conical distal portion 16 of the body (see FIG. 1) comprises surfaces which define with the central axis of L—L of he body an included angle of 45°. The diameter of the proximal cylindrical portion 20 of the plunger is 1.59 inch, the diameter of the distal cylindrical portion 18 of the plunger is 1.405 inch, and the diameter of the intermediate cylindrical portion 24 of the plunger is 1.165 inch. The distal cylindrical portion 20 of the plunger in this illustrative embodiment has an axial thickness of 0.125 inch, the intermediate cylindrical portion 24 of the plunger has an axial thickness of 0.18 inch, and the distal cylindrical portion 18 of the plunger has an axial thickness of 0.12 inch.

In this illustrative embodiment, the axial distance from the proximal face 26 to the bridge segments 36 and 40 bounding respective slot segments 42 and 44, is 0.165 inch. The axial height of the retention members 30 and 32, as measured axially from the rear face 26 of the plunger body, is 0.335 inch and the diameter of the lateral slot comprising slot segments 42 and 44, is 1.04 inch.

In the plunger of the present invention, so long as the central axis of the driving mechanism is coincident with the central axis of the plunger, subsequent rotation of the driving mechanism relative to the plunger will not result in disengagement of the head of the driving mechanism from the plunger. In other words, once the driving mechanism has been brought into initial engagement with the coupling structure of the plunger, any subsequent rotation of the head and shaft of the driving mechanism will not disengage the driving mechanism from the plunger. This retention feature is at odds with the "quick release" structure described in the forementioned Reilly et al U.S. Pat. No. 4,677,980, and achieves a significant advantage thereover, in that the occurrence of vibration, or inadvertent rotation of the head and shaft of the driving mechanism which may cause undesirable (e.g., premature) disengagement of the driving mechanism from the plunger in such prior art system, does not adversely affect the engagement of the coupling structure in the plunger of the present invention.

While the invention has been described with reference to specific embodiments, aspects, and features thereof, it will be appreciated that the invention is not thus limited, in that apparent variations, modifications, and other embodiments will suggest themselves to those of ordinary skill in the art. Accordingly, the invention s to be broadly construed and regarded as encompassing all such alternative variations, modifications, and embodiments.

What is claimed is:

1. A plunger having utility in a power-driven angiographic syringe assembly comprising power driving means including an axially extending drive shaft and a transversely extending driving head attached to said shaft, the plunger comprising:
   a plunger body having a generally convergent distal portion and a proximal face; and
   laterally spaced-apart power driving means retention members each having a leg portion extending generally rearwardly from said proximal face and joined at a rearward part thereof to a bridge segment laterally inwardly extending therefrom toward the other of said retention members to an inner extremity which is in spaced relationship to the corresponding inner extremity of the bridge segment of the other said retention member, with a lateral spacing between the inner extremities of the bridge segments accommodating transverse passage of said drive shaft therethrough, said leg portions and bridge segments of said retention members defining with said proximal face a lateral slot accommodating transverse passage of said driving head therethrough, and transversely outwardly extending flexible, resilient flange elements joined to the inner extremity of each said bridge segment and forming laterally spaced-apart, transversely aligned pairs of said flange elements on either side of said bridge segments, defining a transverse channel therebetween, the flange elements being shaped to define marginal portions of said transverse channel including a reduced channel width relative to a medial portion of said transverse channel, with the marginal channel portions allowing transverse passage of said drive shaft therethrough by deformation of said flange elements bounding said marginal portions, so that the drive shaft thereafter is retentively held in said medial portion of the transverse channel to accommodate free rotation of the driving mechanism relative to the plunger without disengagement of the driving mechanism therefrom.

2. A plunger according to claim 1, wherein the flange elements joined to each said bridge segment define a flattened W-shape when viewed in top plan view of said proximal face of the plunger.

3. A plunger according to claim 1, wherein each said bridge segment and flange elements attached thereto define a flattened wishbone shape when viewed in top plan view of said proximal face of the plunger.

4. A plunger according to claim 1, wherein the flange elements are of serpentine shape in plan view of the proximal face of the plunger, with oppositely facing flange elements bounding the transverse channel defining channel sections including:
   (i) a laterally divergent channel inlet at marginal extremities of the flange elements;
   (ii) a laterally convergent neck section of the channel adjacent said inlet; and
   (iii) a medial, laterally divergent channel section forming said medial portion of the channel.

5. A plunger according to claim 1, wherein the plunger body is formed of a polymeric material.

6. A plunger according to claim 1, comprising a sheath mounted on a distal portion of the plunger body.

7. A plunger according to claim 6, wherein the sheath is formed of a natural rubber material.

8. An angiographic syringe, having a plunger according to claim 1 mounted therein, for axial sliding movement of the plunger in an interior volume of the syringe.

9. An angiographic syringe, comprising a plunger according to claim 1.

10. An angiographic power injector system comprising a driving mechanism including head and shaft elements; and an angiographic syringe comprising a plunger according to claim 1, mounted for selective engagement with the head and shaft elements of the driving mechanism thereof.

* * * * *

UNITED STATES PATENT AND TRADEMARK OFFICE
CERTIFICATE OF CORRECTION

PATENT NO.   : 4,911,695
DATED        : March 27, 1990
INVENTOR(S)  : Thomas A. Lindner It is certified that error appears in the above-identified patent and that said Letters Patent is hereby corrected as shown below:

Column 1, line 40, change "wit" to --with--.

Column 2, line 8, change "he" to --the--.

Column 3, line 43, change "f" to --of--.

Column 5, line 5, change "plunge" to --plunger--.

Column 6, line 1, change "define" to --defined--.

Column 8, line 20, change "he" to --the--.

Column 10, line 31, change "o" to --on--.

Column 11, line 40, change "s" to --is--.

Signed and Sealed this

Sixteenth Day of April, 1991

Attest:

HARRY F. MANBECK, JR.

Attesting Officer

Commissioner of Patents and Trademarks